(12) United States Patent
Pinheiro

(10) Patent No.: US 6,355,056 B1
(45) Date of Patent: *Mar. 12, 2002

(54) IMPLANTABLE INTRALUMINAL PROSTHESIS

(75) Inventor: Orlando S. Pinheiro, Harrison, NJ (US)

(73) Assignee: Meadox Medicals, Inc., Oakland, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/217,654

(22) Filed: Dec. 21, 1998

Related U.S. Application Data

(63) Continuation of application No. 08/701,539, filed on Aug. 22, 1996, now Pat. No. 5,851,228, which is a continuation of application No. 08/456,783, filed on Jun. 1, 1995, now abandoned.

(51) Int. Cl.[7] ................................................. A61F 2/00
(52) U.S. Cl. ..................................... 623/1.13; 623/1.36
(58) Field of Search ................................ 602/108, 191, 602/194, 195, 198; 623/1, 11, 12, 1.1, 1.13, 1.14, 1.35, 1.36

(56) References Cited

U.S. PATENT DOCUMENTS

| 3,657,744 | A | 4/1972 | Ersek |
| 4,140,126 | A | 2/1979 | Choudhury |
| 4,512,338 | A | 4/1985 | Balko et al. |
| 4,562,596 | A | 1/1986 | Kornberg |

(List continued on next page.)

FOREIGN PATENT DOCUMENTS

| EP | 0 539 237 A1 | 10/1992 |
| EP | 0 657 147 A2 | 10/1994 |
| SU | 1457921 A1 | 3/1988 |
| SU | 1457921 | 2/1989 |
| WO | WO 95/09584 | 10/1994 |

*Primary Examiner*—Michael J. Milano
(74) *Attorney, Agent, or Firm*—Hoffmann & Baron, LLP

(57) ABSTRACT

An implantable intraluminal prosthesis assembly is provided for use in repairing or replacing damaged or diseased portions of a blood vessel or other like vessel. The prosthesis includes an expandable stent/graft combination, with a pair of stents at either end of the graft, and further includes a plurality of struts extending between and interconnecting the stents, and radially spaced about the inner surface of the graft. As such, the implantable prosthesis is provided with internal support for the graft when in a compressed state during implantation and is further provided with radial support along the length of the graft after implantation.

12 Claims, 2 Drawing Sheets

U.S. PATENT DOCUMENTS

| | | |
|---|---|---|
| 5,104,404 A | 4/1992 | Wolff |
| 5,122,154 A | 6/1992 | Rhodes |
| 5,133,732 A | 7/1992 | Wiktor |
| 5,135,536 A | 8/1992 | Hillstead |
| 5,195,984 A | 3/1993 | Schatz |
| 5,282,824 A | 2/1994 | Gianturco |
| 5,290,305 A | 3/1994 | Inoue |
| 5,330,500 A | 7/1994 | Song |
| 5,354,308 A | 10/1994 | Simon et al. |
| 5,360,443 A | 11/1994 | Barone et al. |
| 5,382,261 A | 1/1995 | Palmaz |
| 5,387,235 A | 2/1995 | Chuter |
| 5,405,377 A * | 4/1995 | Cragg .......................... 623/1 |
| 5,507,771 A | 4/1996 | Gianturco |
| 5,591,195 A * | 1/1997 | Taheri et al. .................. 623/12 |
| 5,628,783 A | 5/1997 | Quiachon et al. |
| 5,693,085 A * | 12/1997 | Buirge et al. ................ 606/194 |
| 5,713,917 A * | 2/1998 | Leonhardt et al. ............. 623/1 |
| 5,733,325 A | 3/1998 | Robinson et al. |
| 5,800,520 A * | 9/1998 | Fogarty et al. ................. 623/1 |
| 5,961,546 A | 10/1999 | Robinson et al. |

\* cited by examiner

IMPLANTABLE INTRALUMINAL PROSTHESIS

This is a continuation of application Ser. No. 08/701,539, filed Aug. 22, 1996, now U.S. Pat. No. 5,851,228; which is a continuation of application Ser. No. 08/456,783, filed Jun. 1, 1995, now abandoned.

FIELD OF THE INVENTION

The present invention relates generally to an expandable intraluminally implantable prosthesis. More particularly, the present invention relates to a radially supported graft/stent combination which may be intraluminally implanted in a minimally invasive procedure to repair or replace a damaged vessel of the vascular system.

BACKGROUND OF THE INVENTION

It has long been known to employ intraluminally implantable prosthetic devices to repair or replace a damaged or diseased portion of a body lumen such as a blood vessel. Intraluminal implantation in a minimally invasive procedure permits such repair without the necessity of major surgical intervention. Typically, such implantation involves the use of a delivery system employed directly percutaneously or in other minimally invasive procedures, such as cut downs. In this manner, endovascular structures may be implanted by use of such a delivery system from a location remote from the damaged area. Intraluminal implantation in this manner greatly minimizes the risks inherent in major surgical implantation as it is less traumatic, less complicated, and generally a safer procedure. The prosthesis so delivered establishes a conduit which bridges the damaged portion of the vessel, thereby re-establishing blood flow therethrough without risk of further damage to the vessel. While vascular repair is one of the more common applications of an intraluminal prosthesis, such prosthesis may also be designed for use in other body lumens where repair is required.

The art has seen a wide variety of intraluminally deliverable prosthetic devices. Typically, these devices may include a tubular graft which is designed to span the damaged site of the vessel to permit blood flow therethrough. Such a graft is generally a compressible, flexible member which may be compressed or compacted into a small configuration so as to permit intraluminal delivery. In order to securely anchor the graft in place, the prosthesis may also include one or more stents attached to the graft itself. A stent is a compressible spring-like member which may be self-expanding such that when the prosthesis is deployed at its proper location, the stent expands so as to expand the graft into contact with the lumen to be repaired. The stent also serves to anchor the graft in place, thereby preventing migration of the prosthesis once the prosthesis is properly implanted.

An endovascular prosthesis employing a graft/stent combination which may be deliverable intraluminally via a delivery catheter is shown and described in U.S. Pat. No. 5,387,235, issued to Chuter. This patent describes a radially self-expandable prosthesis, including a woven, multi-filament polyester tubular graft which is supported by a spring assembly. The spring assembly includes individual stents at each end of the graft. A sheath is used to hold the graft and stents in a compressed condition so that it may be delivered intraluminally via the delivery catheter. Once properly located, the sheath is removed and the prosthesis is allowed to self-expand within the vessel across the damaged area. The individual stents may include outwardly directed barbs which anchor into the vessel securely positioning the prosthesis and preventing migration thereof.

The apparatus described in the '235 patent serves adequately to implant a prosthesis intraluminally across a damaged vessel. However, as the graft is supported at spaced apart opposite ends thereof by the individual stents, the central portion of the graft is unsupported. Such unsupported central extent is subject to collapsing, kinking or folding, especially as the prosthesis traverses a tortuous path during implantation. Also, as separate spaced apart stents are employed at each end of the graft, it is possible for the stents to migrate axially relative to one another during implantation.

One attempt to address problems such as these in a percutaneously implantable prosthesis is shown in U.S. Pat. No. 5,282,824, issued to Gianturco. A graft/stent combination is disclosed where the spaced apart stents supporting opposed ends of the graft are connected by a single elongate rod. The single rod is designed to resist the contraction of the assembly along the longitudinal axis when the assembly is radially compressed and/or expanded. While the design of the stent assembly of the '824 patent serves to maintain axial spacing between the spaced apart stents, the single rod connecting the stents offers little or no radial support to the graft positioned thereover. Thus, the prosthesis of the '824 patent is still subject to kinking, collapsing or folding during and after implantation.

It is therefore desirable to provide a prosthesis including a stent/graft combination which provides adequate radial support from within the graft to maintain the graft in expanded condition without risk of collapsing, kinking or folding.

SUMMARY OF THE INVENTION

It is an object of the present invention to provide an implantable prosthetic device which may be implanted intraluminally without need for major surgical intervention.

It is a further object of the present invention to provide an intraluminally implantable stent/graft combination for use in repairing a damaged blood vessel.

It is a still further object of the present invention to provide an intraluminally implantable, self-expanding stent/graft combination which provides radial support for the graft so as to resist collapsing, kinking and folding during and after implantation.

In the efficient attainment of these and other objects, the present invention provides an implantable assembly. The assembly includes an elongate, generally tubular compressible graft having opposed end portions. A pair of resiliently compressible, generally tubular stents are positioned within the graft at spaced apart locations adjacent the end portions of the graft. A plurality of elongate struts extend between and interconnect the stents. The struts are radially spaced about the inner cylindrical surface of the graft and are designed for contact therewith, so as to provide internal radial support to the graft when in a compressed state and to further provide radial support along the length of the graft after implantation.

As more particularly described by way of the preferred embodiment herein, the graft is generally a textile graft having opposed open ends. A pair of stents, each formed by wire portions arranged in a zig-zag configuration, are disposed at the open ends of the graft. At least four struts are provided to span the central portion of the graft and interconnect the two stents. The struts are spaced such that they provide internal support for the graft, resisting kinking, collapsing or folding of the graft and also are spaced and arranged in such a manner that thrombosis formation between the struts is reduced.

DETAILED DESCRIPTION OF THE INVENTION

Figure 1:
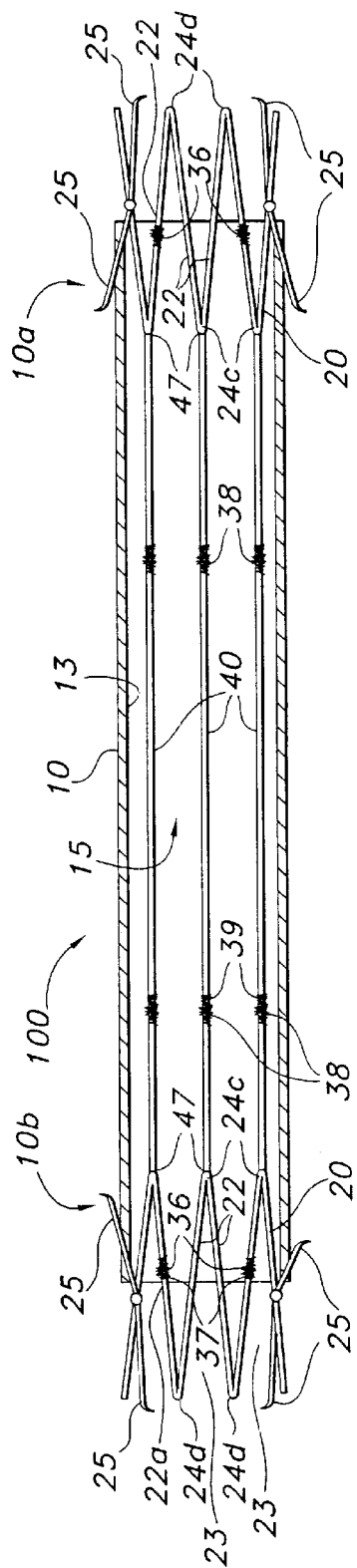
FIG. 1 shows, in longitudinal cross-section, the expanded intraluminal prosthesis of the present invention.

The present invention is directed to an implantable assembly for a diseased or damaged portion of a blood vessel or other like vessel to provide replacement or reinforcement of the damaged vessel. Such an implantable assembly is typically referred to as a prosthesis. Referring to FIG. 1, the prosthesis of the present invention is shown generally at prosthesis 100. Prosthesis 100 includes elongate, generally tubular graft 10. Graft 10 may be any conventional graft constructed of any material known in the art. For example, graft 10 may be a textile member, constructed of braided, knitted or woven synthetic yarns such as polyester, or may be formed of an extruded plastic such as expanded polytetrafluoroethylene (PTFE). Graft 10 is compressible in order to permit implantation via a delivery catheter.

Graft 10 includes first open end portion 10a and second open end portion 10b opposed thereto. The tubular shape of graft 10 between first open end portion 10a and second open end portion 10b is defined by the wall of graft 10 which includes inner surface 13. The tubular shape of graft 10 defines inner lumen 15, which is designed to permit, for instance, blood flow therethrough upon implantation.

Figure 2:
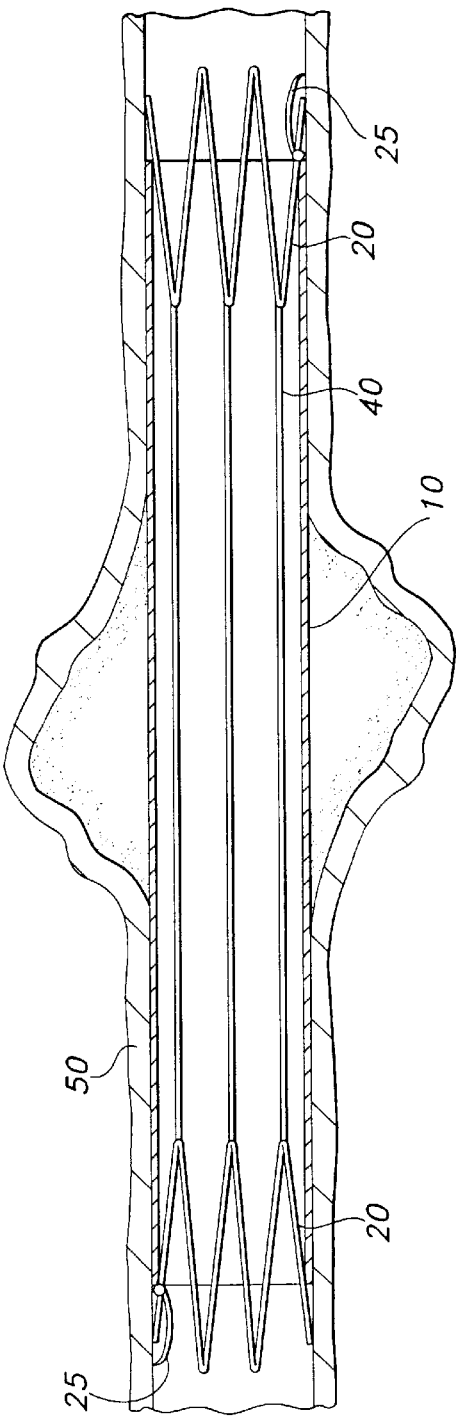
FIG. 2 shows, in longitudinal cross-section, the prosthesis of FIG. 1 implanted in a blood vessel.
Figure 3:
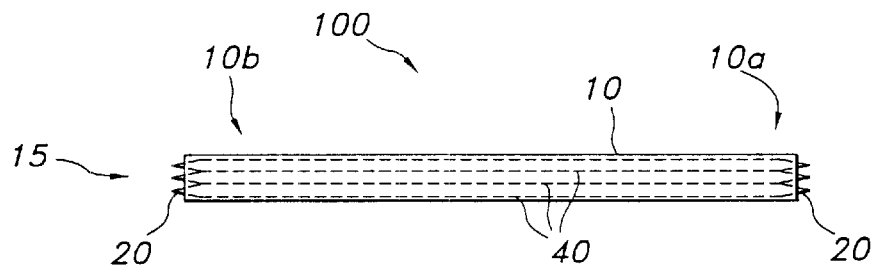
FIG. 3 shows the prosthesis of FIG. 1 in compressed condition for implantation in a delivery catheter.

A pair of resiliently compressible, generally tubular stents 20 are positioned within graft 10 at spaced apart locations adjacent first open end portion 10a and second open end portion 10b. Stents 20 may be any type of stents known for such applications in the art, and may be constructed of any material known in the art, such as stainless steel or other metals or alloys, polymeric materials, or composites of polymers and metal. Preferably, stents 20 are constructed of stainless steel wire. In operation, stents 20 maintain graft 10 in expanded position against the wall of blood vessel 50, as depicted in FIG. 2. The present invention contemplates use of any type of expandable stents known in the art, for instance, self-expandable stents, balloon-expandable stents, temperature-expandable stents, and the like. In the preferred embodiments shown herein, stents 20 are of the self-expandable type being expandable in a radial direction between a compressed diameter and a larger expanded diameter. Stents 20 are formed in a closed zig-zag configuration, commonly referred to as Z-stents. Such Z-stents are commonly known in the art, and are further described in U.S. Pat. No. 4,580,568 to Gianturco, incorporated herein by reference.

Stents 20 may be secured to inner surface 13 of graft 10. Preferably, this securing is accomplished by stent sutures 36, which may be any suture known in the art. Stent sutures 36 are provided in order to maintain stents 20 in a position adjacent first open end portion 10a and second open end portion 10b of graft 10. Stent sutures 36 may be attached to stent 20 at raised stent coils 37, which are capable of accommodating stent sutures 36 and preventing movement of the stent 20 with respect to the graft 10.

Figure 4:
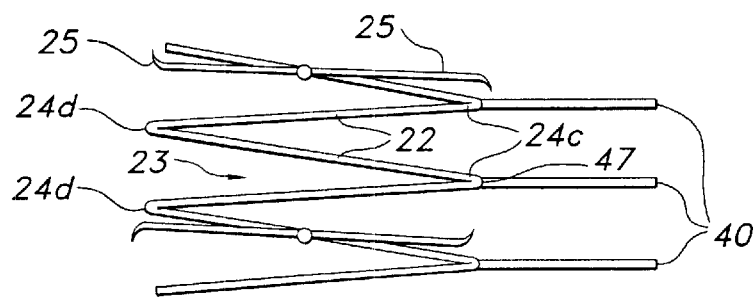
FIG. 4 is an enlarged plan view of a portion of a stent of the prosthesis of the present invention.

As mentioned above, stents 20 are formed in a zig-zag configuration, as further depicted in FIGS. 1 and 4. With such a configuration, stents 20 are formed of wire defining a plurality of wire extents 22, with spaces 23 between adjacent wire extents 22. Wire extents 22 may exist as discrete members, with adjacent wire extents 22 being connected to one another at stent joints 24c and 24d. In such a configuration, stents 20 are typically positioned at first open end portion 10a and second open end portion 10b of graft 10 such that a portion of stents 20 exists within inner lumen 15 of graft 10 and a portion of stents 20 exists outside of inner lumen 15 of graft 10. In this manner, internal stent joints 24c are positioned within inner lumen 15 and external stent joints 24d are positioned outside of inner lumen 15. It should be noted that in this arrangement, "internal" is being used to designate a general area toward the central or medial area of implantable assembly 100, while "external" is being used to designate a general area extending distally beyond the end portions of implantable assembly 100. In such a configuration, it is preferable that stent sutures 36 securing stents 20 to graft 10 are positioned generally at intermediate portion 22a of selected ones of wire extents 22 to provide effective securement.

It is further contemplated that stents 20 may include anchoring barbs 25 attached thereto. Such anchoring barbs 25 are commonly known and used in combination with stents and are capable of engagement with blood vessel 50 to assist in anchoring prosthesis 100 in place within blood vessel 50 after implantation. Anchoring barbs 25 are attached to selected ones of wire extents 22 and extend outside of inner lumen 15 of graft 10 to a position proximate to and adjacent internal stent joints 24c and external stent joints 24d, as depicted in FIG. 4. Preferably, anchoring barbs 25 are attached generally to intermediate portion 22a of selected ones of wire extents 22, and extend outside of graft 10. In this manner, anchoring barbs 25 provide an effective medially balanced anchoring means for anchoring prosthesis 100 within blood vessel 50, as depicted in FIG. 2.

As shown in FIG. 1, prosthesis 100 further includes a plurality of struts 40 extending between and interconnecting stents 20. Struts 40 are radially spaced about inner surface 13 of graft 10, and positioned for contact with graft 10. Preferably, struts 40 are equally radially spaced about inner surface 13 of graft 10. This positioning provides effective internal support for graft 10 when in a compressed state and further provides radial support along the length of graft 10 when in an expanded state after implantation. Struts 40 may be constructed of any material known in the art, such as stainless steel or other metals or alloys, polymeric materials, or composites of polymers and metal. Preferably, struts 40 are constructed of similar material to stents 20, and in most preferred embodiments, both stents 20 and struts 40 are constructed of stainless steel wire.

Struts 40 extend generally parallel with inner lumen 15 of graft 10, and therefore parallel with the direction of blood flow therethrough, as depicted in FIG. 1. Such an arrangement provides effective support for graft 10 while reducing the likelihood of thrombosis from occurring within graft 10.

In the preferred embodiment shown herein, prosthesis 100 includes four struts 40 substantially equally radially spaced about inner surface 13 of graft 10. With four struts 40 provided in this manner, graft 10 is provided with sufficient radial support during and after implantation, with the likelihood of thrombosis formation being reduced.

Optionally, struts 40 may also be directly secured to graft 10 using stent sutures 38. Each strut 40 may include spaced apart raised strut coils 39 therealong. These raised strut coils 39 which are similar to stent coils 37 described above, may accommodate strut sutures 38 in a manner shown in FIG. 1. The engagement of strut sutures 38 with strut coils 39 helps maintain the position of graft 10 about struts 40 and to further provide effective securement and support for graft 10.

Struts 40 may be attached at both ends to internal stent joints 24c by any known means of attachment. Preferably, struts 40 are soldered to internal stent joints 24c, as depicted in FIGS. 1 and 4 at solder joint 47. This attachment of struts 40 to internal stent joints 24c provides for effective support within prosthesis 100, and ensures that a proper distance will be maintained between stents 20, thereby preventing migration of the stents during and after implantation. In the preferred embodiments, struts 40 are attached to internal stent joints 24c that do not have an anchoring barb 25 extending proximate and adjacent thereto.

While four equally spaced struts 40 are shown herein, the present invention contemplates use of differing numbers of plural struts. The number of struts employed in each particular instance may vary with the particular construction of stents 20. The struts 40 may be provided in one-to-one correspondence with the number of internal stent joints 24c (FIG. 4), so that one strut 40 extends from each internal stent joint 24c. Alternatively, the struts 40 can extend from every other internal stent joint 24c so that the number of struts 40 will be one-half the number of internal stent joints 24c of each stent. While three or four stents are contemplated as the minimum number needed to provide sufficient radial support for grafts 10, a greater number of struts may also be employed.

Figure 5:
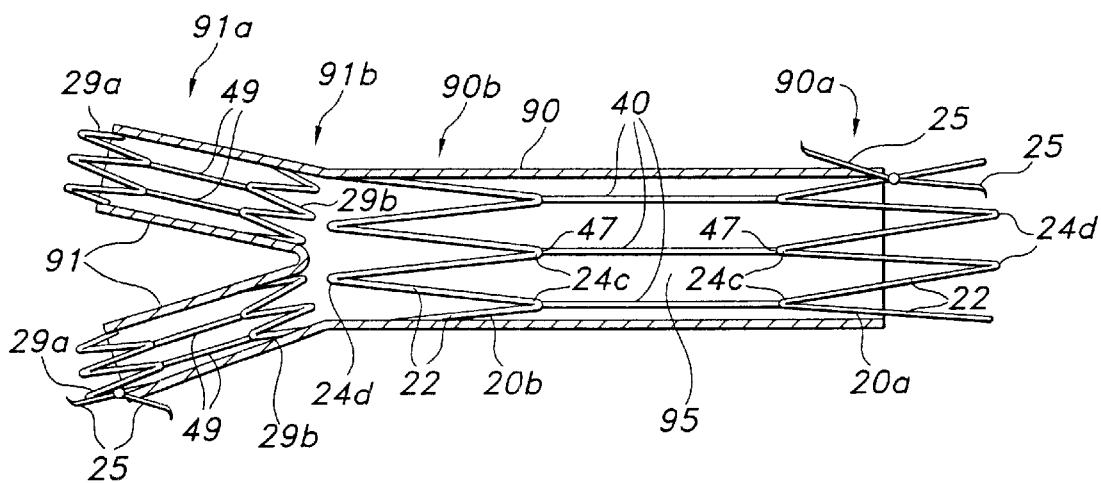
FIG. 5 shows, in longitudinal cross-section, a bifurcated prosthesis of the present invention.

In a further embodiment of the present invention as depicted in FIG. 5, a bifurcated graft 90 is provided. Bifurcated graft 90 includes first open end portion 90a and second end portion 90b, with a pair of tubular legs 91 extending from second end portion 90b. Tubular legs 91 include leg open end portions 90a and leg attached portions 90b, with a path of communication for blood flow from inner lumen 95 through both tubular legs 91 and through leg open end portions 90a. Such bifurcated grafts are commonly known in the art and are commonly used in implantation procedures.

In such an embodiment, stent 20a exists adjacent first open end portion 90a and a second stent 20b exists adjacent second end portion 90b, with struts 40 extending therebetween in a manner similar to that described above. However, it should be noted that in this embodiment, stent 20b which is positioned adjacent said second end portion 90b is positioned entirely within inner lumen 95 of bifurcated graft 90. Such positioning would obviate the need for anchoring barbs thereon.

In the instant embodiment, an additional pair of resiliently compressible, generally tubular spaced apart leg stents 29a and 29b of the type similar to stents 20, described above, may be provided within each of tubular legs 91 adjacent leg open end portions 90a and spaced from second end portion 90b of bifurcated graft 90. Such additional leg stents 29a and 29b maintain tubular legs 91 in contact with blood vessel 50 in a similar manner as stents 20a and 20b. Leg stents 29a may include anchoring barbs 25 to anchor leg stents 29a to the blood vessel in a manner similar to the preferred embodiment. Further, additional struts 49 may be included within tubular legs 91. Additional struts 49 are attached at both ends between leg stents 29a and 29b as shown in FIG. 5. Each pair of additional struts 49 extends between each pair of leg stents 29a and 29b. Additional struts 49 function in a similar manner to struts 40 in the main body portion of bifurcated graft 90 in that they provide radial support to the tubular legs 91.

The prosthesis of the present invention can be implanted into the body using any known method of implantation, for instance, transcutaneous implantation, percutaneous implantation, cut down procedures, and the like. Preferably, the present inventive prosthesis is utilized with a deployment system capable of minimally invasive transcutaneous insertion. Such deployment systems are known in the art and are described in U.S. Pat. No. 5,387,235 to Chuter, incorporated herein by reference.

While the invention has been described herein in terms of certain preferred embodiments, those skilled in the art will recognize that various modifications can be made without departing from the scope of the present invention.

What is claimed is:

1. An implantable assembly comprising:
    an elongate, generally tubular compressible graft having opposed end portions,
    a pair of resiliently compressible, generally tubular wire stents of generally zig-zag configuration positioned within said tubular graft at spaced apart locations adjacent said end portions of said graft said stents having radially spaced medial and distal stent joints; and
    a plurality of elongate struts extending between and interconnecting said stents at alternating ones of said medial stent joints, said struts being radially spaced about the inner surface of said graft and being secured directly thereto to provide internal support to said graft when in a compressed state and to further provide radial support along the length of said graft after implantation.

2. An implantable assembly of claim 1 further including means for securing said stents in said graft adjacent said ends thereof.

3. An implantable assembly of claim 2 wherein said securing means includes said stent being sutured to said graft.

4. An implantable assembly of claim 1 wherein said graft is a textile graft.

5. An implantable assembly of claim 1 wherein said stents are self-expanding stents.

6. An implantable prosthesis comprising:
    an elongate, radially compressible tubular graft having an inner tubular surface, said graft having opposed first and second open end portions; and
    a stent assembly supported within said tubular graft, said stent assembly comprising:
        a first generally tubular radially self-expanding stent supported within said graft adjacent said first open end portion;
        a second generally tubular radially self-expanding stent supported within said graft adjacent said second open end portion; and
        a plurality of elongate struts extending between and interconnecting said first and second stents, said struts being radially spaced about said inner tubular surface of said graft, said struts further including at least one strut coil at an intermediate location with said strut, coil being in direct secured contact with said graft for providing internal support to said graft.

7. A prosthesis of claim 6 wherein said plurality of struts includes at least four struts substantially equally radially spread about said inner tubular surface of said graft.

8. A prosthesis of claim 7 wherein said stents and said struts are formed of metallic wire.

9. An implantable prosthesis of claim 6 wherein said at least one strut coil is secured to said graft with strut sutures.

10. An implantable prosthesis of claim 6 wherein each of said struts includes plural spaced apart strut coils.

11. An implantable graft/stent composite prosthesis comprising:
    an elongate generally tubular graft having opposed ends;
    a plurality of stents positioned within said tubular graft at spaced-apart locations; and
    at least one elongate strut interconnecting said stents, said strut including at least one strut coil located intermediate said stent and being sutured to said graft.

12. An implantable graft/stent composite prosthesis of claim 11 wherein said elongate strut is secured to said graft at spaced-apart locations therealong.

* * * * *